United States Patent [19]

Smith et al.

[11] Patent Number: 5,500,954
[45] Date of Patent: Mar. 26, 1996

[54] SAFETY SHIELD SYSTEM

[75] Inventors: Jack V. Smith, St. Petersburg; Jesse M. Carter, Tampa, both of Fla.

[73] Assignee: J. Prime Industries, Inc., St. Petersburg, Fla.

[21] Appl. No.: 236,656

[22] Filed: Apr. 29, 1994

Related U.S. Application Data

[63] Continuation of Ser. No. 970,037, Nov. 2, 1992, abandoned.
[51] Int. Cl.$^6$ .............................. A41D 13/00; A61F 9/04
[52] U.S. Cl. ............................................................ 2/9
[58] Field of Search ............................ 2/9, 11, 4, 15, 2/424, 8; 128/857, 201.24, 206.21

[56] References Cited

U.S. PATENT DOCUMENTS

| | | | |
|---|---|---|---|
| 1,265,764 | 5/1918 | Ferrara | 2/11 |
| 1,561,760 | 11/1925 | WhelaN | 2/11 |
| 1,906,539 | 5/1933 | Church | 2/11 |
| 2,564,952 | 8/1951 | Blasius | 2/11 |
| 3,423,763 | 1/1969 | Schwartz | 2/9 |
| 4,286,170 | 8/1981 | Moti | 2/9 |
| 4,986,282 | 1/1991 | Stackhouse et al. | 2/410 |

FOREIGN PATENT DOCUMENTS

| | | | |
|---|---|---|---|
| 554746 | 2/1957 | Belgium | 2/9 |
| 268624 | 6/1989 | Germany | 2/9 |
| 458636 | 7/1950 | Italy | 2/9 |
| 1007197 | 10/1965 | United Kingdom | 2/11 |

OTHER PUBLICATIONS

"The Optician", vol. 152, No. 3949, p. 585, Dec. 9. 1966.

*Primary Examiner*—Michael A. Neas
*Attorney, Agent, or Firm*—Herbert W. Larson

[57] ABSTRACT

A safety system shield which protects the head, facial, throat, and upper thorax regions of the body from exposure to biological, chemical, and physical matter that may take the form of solids, liquids, or aerosols, and includes a thin flexible shield which is curved, and transparent. It is shaped to rest on the anterior shoulder, and thorax region of the body, thereby allowing the head to look in any direction. This relieves the wearer's head of the weight of the shield while affording maximum protection. The safety shield system is ultra-light weight thus, reduces wearer's fatigue, and eliminates headaches, resulting in the enhancement of safety, and the reduction of accidents. The safety shield is flexible allowing it to conform to the size, and curvature of the wearer.

1 Claim, 4 Drawing Sheets

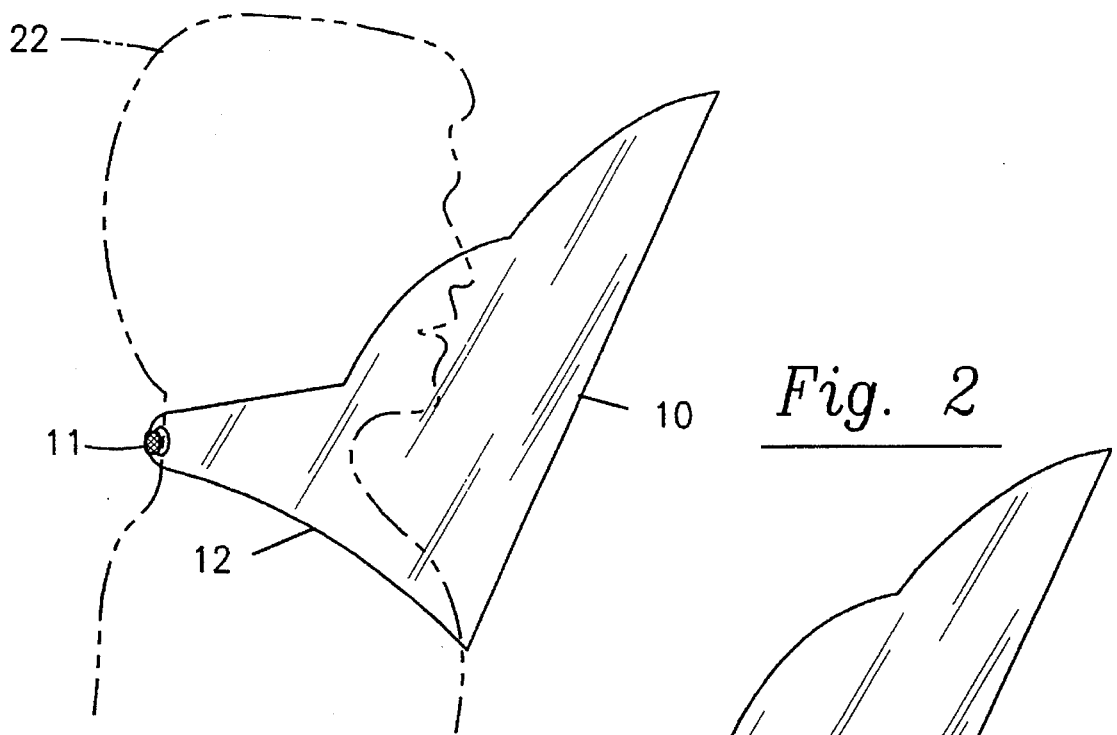
*Fig. 1*
*Fig. 2*
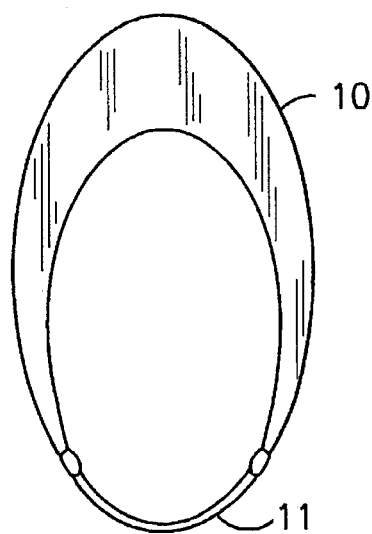
*Fig. 3*
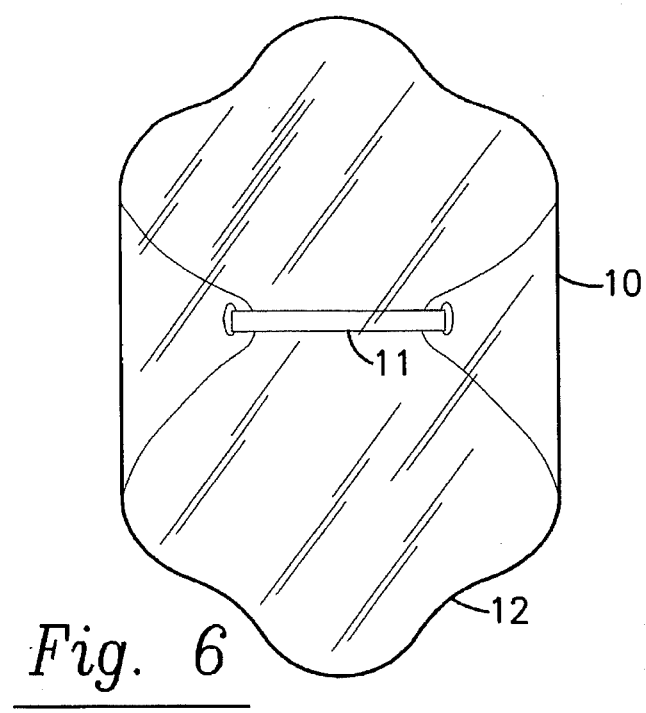
*Fig. 6*

SAFETY SHIELD SYSTEM

This is a continuation of Ser. No. 07/970,037, filed Nov. 2, 1992, now abandoned.

BACKGROUND OF THE INVENTION

This invention relates to a safety shield system that is designed for use in protecting an individual's upper torso, neck, and head region from biological, chemical, or solid matter while allowing the user free use of his, or her hands. This invention is worn by the user, and provides the same protection previously afforded only by bench-mounted stationary shields, but does not restrict the movements of the user. This device is flexible, allowing it to conform to the contours, and dimensions of the wearer. It can be disinfected when exposed to infectious materials, or disposed of. This invention is superior to prior art (face shields) due to the inclusion of previously unprotected areas, and the elimination of headaches due to cranial pressure resulting from the weight of head mounted face shields.

Today's environment presents an increased risk to the health care worker in the form of life threatening viruses (e.g. AIDS, Hepatitis, etc.) transmitted via blood, infectious materials, and other body fluids. This is a public concern, because of its negative impact on the economy, general well-being, and the health of the community at large. The issue of public health hazards can be addressed by reducing the risk of exposure to the worker in the health care field. According to the Occupational Safety and Health Administration (OSHA) more than 5.6 million workers in the health care and public safety occupations could be potentially exposed to these viruses.

With the inception of the recent OSHA standard, Part 1910.1030 of Title 29 of the Code of Federal Regulations, an acknowledgment is made of the potential danger due to bloodborne pathogens and the many pathways of exposure to healthcare professionals. One section of the standard states that personal protective equipment (e.g. gloves, face shields, etc.) is considered appropriate only if it does not permit blood or other potentially infectious materials to pass through or reach employee's work clothes, street clothes, skin, eyes, mouth, or other mucous membranes under normal condition of use and for the duration of time which the protective equipment will be used. It should be further noted that any protective device must be worn to be effective. A safety shield which causes physical discomfort, or significantly affects the ability of the worker to perform required tasks will not be fully utilized. In view of the foregoing facts the health care worker should be afforded the most encompassing protection available while providing comfort, unobstructed vision, and mobility.

Another aspect of this invention is the protection provided by the use of this device to the industrial worker and hobbyist. By wearing this shield during operations such as grinding, welding, sawing and other related activities a more complete protection is provided than that currently available via prior art. In the prior art associated with facial safety shields used in the health care field several designs have been patented. U.S. Pat. No. 4,986,282 is delineated as a face shield system having a support that is adjustable to fit on the head of the user which includes a horizontal headband section as an integral part of said support member. Therefore, this face shield is supported by the head and neck contributing to worker fatigue and unnecessary stress resulting in eye strain, head-aches, and the like. A major contributor of the pressure, and stress (causative factor of headaches etc . . . ) is that all prior art uses a 'lip' to extend the shield face a few inches beyond the eyes of the user. This lip acts as a fulcrum using the weight of the shield to pull itself off of the head of the user. As a result of this downward force the headband (circling the cranium) which the prior art uses to keep said shield on wearer's head must be tightened, thus applying a constricting force to the head of the user yielding pain, headaches, and fatigue. As stated in prior art U.S. Pat. No. 3,955,570. worker fatigue results in increased industrial accidents, and can be avoided by wearing a light-weight face protection system not supported by the head. The ANSI Z-87.1 Standards, and related studies bear out the evidence concerning worker fatigue resulting from the weight bearing load that the head, and neck are subject to with the prior art.

The prior art, U.S. Pat. No. 4,975,981 and U.S. Pat. No. 4,986,282, states the limited ability of those shields to prevent objects (liquid, solid, etc.) from striking the face, if the said objects are traveling in a straight line (such that the shields are in a vertical position in relation to the projectile) toward the face. Thus, the only protection provided by the prior art is in the immediate facial area (oral cavity, nose, and eyes), if the user's face is in proper orientation (angle) to the incoming objects (i.e. directly in front, and at eye level). This limited protection does not shield the user from objects that can come from other directions such as bench top level (from waist level and up), the side of the head at eye level, or below (to include cheeks, ears, and temple regions), and other anterior, or peripheral angles which might strike the upper thorax, and throat region.

There is no indication in any prior art of a face shield system which would protect the user from exposure to projectiles coming from the aforementioned angles (preceding paragraph). It is undoubtedly clear that a more comprehensive protection that would include previously unprotected areas of the body, greater comfort, and ease of use would warrant significant progress in the science of safety equipment.

In agreement with the present device, a significant improvement for a more comprehensive facial, and upper body protection system is furnished whereupon a safer environment is made available to the health care worker, hobbyist, and industrial employee. The protection afforded by the safety shield is from biological, chemical, and physical matter which may take the form of, but is not limited to liquids, solids, and aerosols.

SUMMARY OF THE INVENTION

In retrospect this invention is the answer to many of the problems unanswered by the prior art as to a full facial, and upper thorax region protection system while providing superior freedom of movement, and ease of use for the health care worker, hobbyist, and industrial employee. The only protection which is now available to the above-mentioned worker that is comparable to this invention is a stationary bench-mounted shield. The clear cut object of the present invention is to provide a more comprehensive shielding system which would make available a wider range of protection to include previously unprotected regions of the face, head, throat, and thorax region of the body from biological, chemical, and physical hazard exposure while allowing for freedom of movement, ease of use, and reduction in worker fatigue, and stress among some of its benefits.

An additional object of this invention is to make available an advanced, simple protection system encompassing the full anterior range of the face, and upper body of the user that shields the user from biological, chemical and physical hazards. The protection afforded by this art is significantly Greater than currently available face shields which only protect eye, nose, and mouth regions.

Additionally, the object of this invention is to provide a comprehensive shielding system that is disposable, and yields the more extensive protection only previously provided by bench mounted shields while retaining the unrestricted mobility and freedom of movement afforded by facial shields yielding less extensive protection.

Another object of this invention is to provide superior, and unmatched facial, and upper thorax protection while allowing complete freedom of movement.

Still another object of this invention is to make wearing the device much less restricting, and cumbersome (due to its flexible conformance to the size, and shape of the wearer) than previous art which only protects the eyes, nose, and mouth.

Adjunctly, the object of this invention is to reduce fatigue, and stress of the wearer by completely removing the weight-bearing load applied to the upper cranial region used by presently available face shields, and goggles. By removing the above-referenced weight, and pressure applied to the head of the wearer, this invention eliminates the occurrence of headaches, and discomfort associated with the system of support utilized by the prior art. The resulting increase in comfort will yield increased utilization of safety shielding thereby making a positive impact on the overall safety in the workplace, and the well-being of workers, and hobbyists. The best safety device is one that is utilized often, and consistently.

Additionally, the object of this invention is to make available an advanced facial, and upper thorax protection system which provides complete encompassing protection that shields the user from objects that can come from directions oriented, in front of the shield at eye level (e.g. oriented vertically, and directly in front at eye level to the shield), which is the only protection afforded by face shields, and goggles. This device will not only provide the aforementioned protection, but also makes available shielding from projectiles that come toward the wearer at bench top level (from waist level, and up), the side of the head at eye level, or below (to include cheeks, ears, and temple areas), and other anterior angles which might strike the upper thorax, and throat region. The aforementioned projectiles may include, but are not limited to biological, chemical, and physical matter that may take the form of solids, liquids, or aerosols.

Another benefit of this invention lies in the fact that it does not restrict the vision (e.g. above eye level, or peripheral), or the mobility of the wearer as does prior art. These features greatly improve the safety factor by improving the range of vision, and movement of the wearer.

Another object of this invention is to provide peripheral protection to the regions along the side of the cranium, and neck left unprotected by previous face shields.

Still another object of this invention is to afford complete freedom of movement of the head, and neck to turn in any orientation to the shield, and still be afforded the complete protection of the shield versus the user of a face shield who loses protection from incoming matter when the wearer looks anywhere, but directly at the source matter.

In addition, the user of the present invention is allowed to look straight ahead, or turn the head in any orientation away from the incoming matter while wearing this invention, and still have the comprehensive protection to include shielding from projectiles that come toward the wearer at bench top level (from waist level and up), the side of the head at eye level, or below (to include cheeks, ears, and temple regions), and other anterior angles which might strike the upper thorax and throat region. The aforementioned projectiles may include, but are not limited to biological, chemical, and physical matter that may take the form of solids, liquids, or aerosols.

An object of this invention is that it can be adapted to any individual for use regardless of size, and shape of user's head or body; in short, one size fits all.

In conjunction with the aforementioned features, the object of this invention is to provide the maximum protection by a shield that is not connected directly to the head in any manner, thus allowing full mobility of the head, and freedom of movement.

In accordance, this invention, a safety shield system which protects the head, facial, throat, and upper thorax regions of the body from exposure to biological, chemical, and physical matter that may take the form of solids, liquids, or aerosols, includes a thin, flexible shield which is curved, and transparent. It is shaped to rest on the anterior shoulder, and thorax region of the body thereby allowing the head to move in any direction without the encumbrance of the head-mounted face shield while affording maximum protection. This aspect of the design eliminates headaches, and fatigue associated with head-mounted shields found in previous art, because the weight bearing load is not supported by the head. This results in enhanced safety, and a reduction in accidents. The safety shield is flexible allowing it to conform to the size, and curvature of the wearer. The upper, and lower portions of the shield are shaped such that they provide protection to the user's head, face, throat, and upper thorax from any projectiles coming toward the wearer from any anterior angles (inclusive of upper, and lower), and/or side angles. This shield is shaped longitudinally such that it will extend from the mid-thorax region to beyond the top of the head of the wearer. Additionally, this shield is shaped horizontally such that it will extend coverage from side to side up to, and beyond the ears of the wearer's head. The invention is held in place by a connective member which rests on the neck and/or shoulders of the wearer. This connective member can include, but is not limited to, an adjustable elastic band, hook and loop material, solid continuation of the shield material, or any other device which will hold said shield in place.

The aspects of the present invention are believed to be novel, and are set forth with particularity in the claims of the invention. If objects of the present invention are not made obvious from the above, they may best be understood from a review of the drawings, and the description of the preferred embodiment which follows.

BRIEF DESCRIPTION OF THE DRAWINGS

FIG. 1 is a perspective view of the safety shield system according to the present invention;

FIG. 2 is a top planar view of the safety shield system of FIG.1;

FIG. 3 is a side angle of elevation view of the safety shield system of FIG. 1;

FIG. 6 is a bottom planar view of the safety shield system of FIG. 1;

DESCRIPTION OF THE PREFERRED EMBODIMENT

As illustrated in FIG. 1, the safety shield system is composed of two separate components: a flexible transparent shield 10, and an adjustable strap 11.

The safety shield system 10 is made up preferably of clear, transparent polycarbonate that is ultra-lightweight. The adjustable strap 11 is preferably made of an adjustable hook, and loop material, and contributes to ease of donning, and doffing of the safety shield 10. In addition, unfastening the adjustable strap 11 is not necessary for removal of the shield, thus the safety shield 10 can be quickly removed if required. The flexibility, and shape of the lower section of the shield 12 makes the safety shield 10 easily adaptable to any individual for use regardless of size, and shape of the user's head, or body.

When worn, the circular shape of the safety shield 10 as illustrated in FIG. 3, provides encompassing protection that shields the user from objects that can come from all directions including those from angles other than directly in front of the shield (this peripheral protection is afforded to the side of the cranium, neck, and upper thorax).

Figures 4, 5:
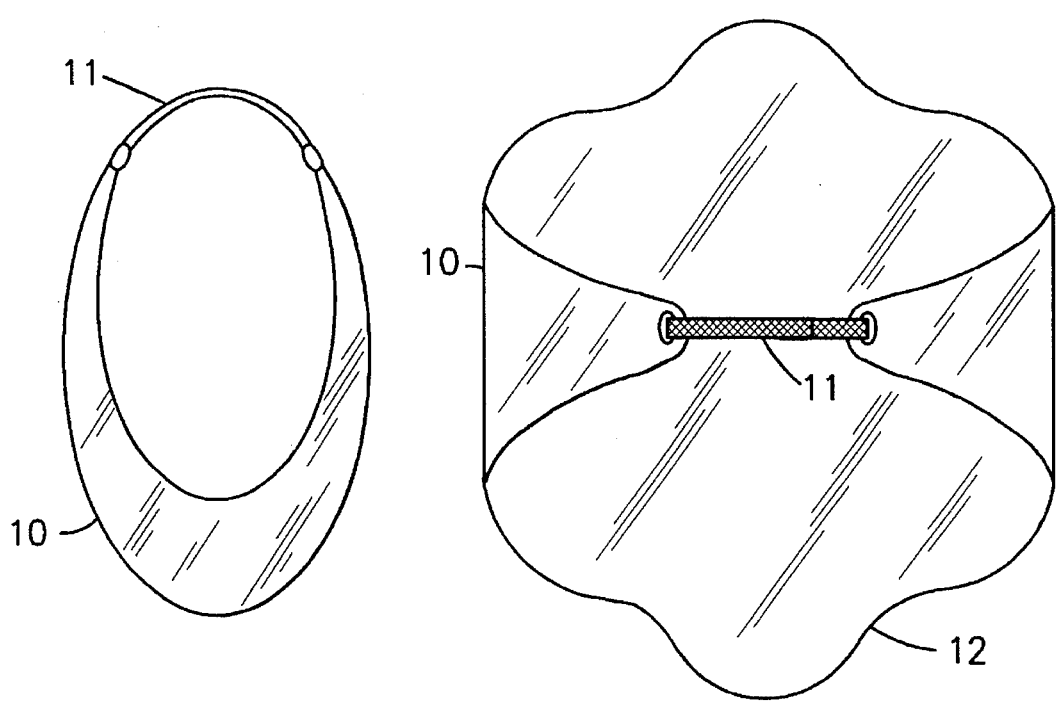
FIG. 4 is a rear angle of elevation view of the safety shield system of FIG. 1.
FIG. 5 is a front angle of elevation view of the safety shield as shown in FIG. 1.
Figure 7:
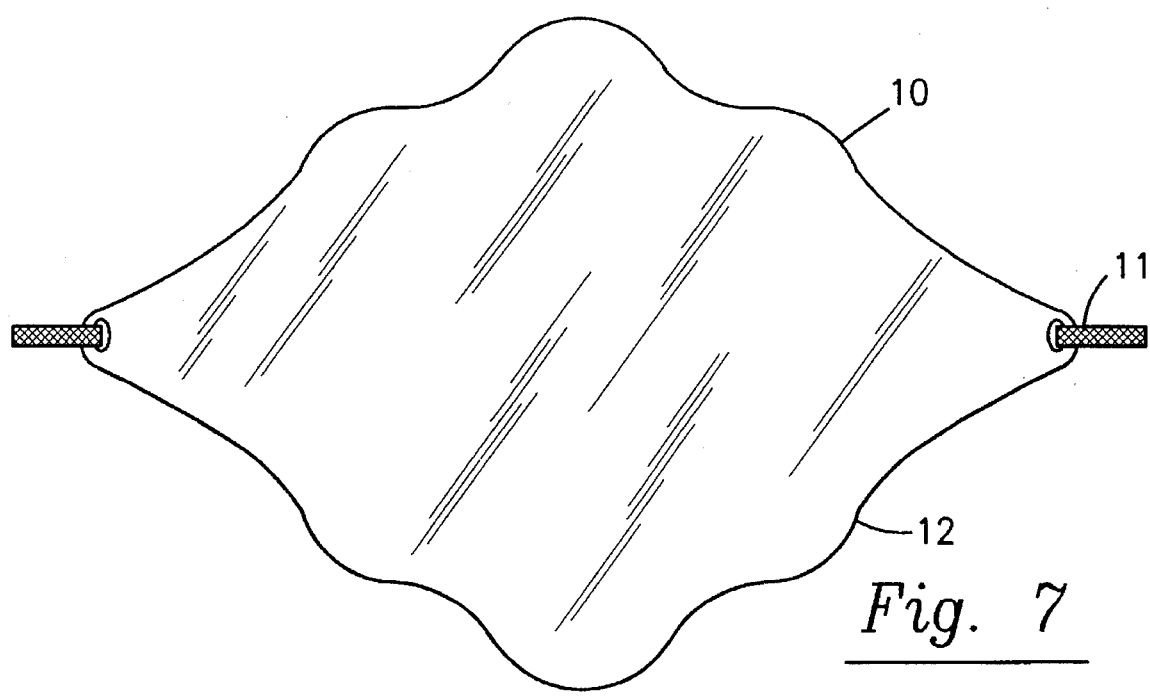
FIG. 7 is a perspective plane view of the safety shield system lying flat on a planar surface.
Figure 8:
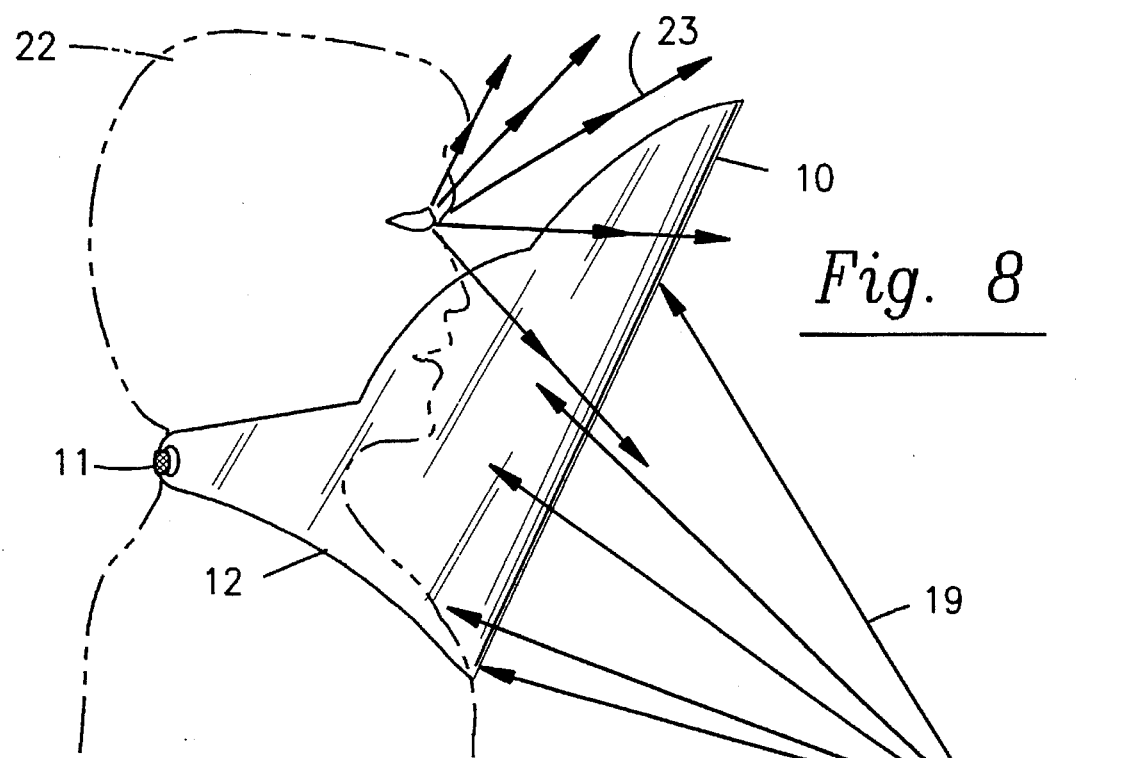
FIG. 8 and FIG. 9 are perspective views showing the relationship between FIG. 8, the safety shield system, and FIG. 9, a face shield system of prior art, demonstrating available protection from projectiles coming from various angles.

FIG. 8 demonstrates the safety shield's 10 ability to allow complete freedom of movement of the head, and neck of the user 22 (as illustrated by the dotted line) to turn in any orientation to the shield, and still be afforded the complete protection of the safety shield 10. The opposite is true for the user 22 of a face shield (previous art) 13 who loses protection from incoming matter when the user 22 looks anywhere, but directly at the source 18 of the incoming projectiles 19. Note, FIG. 8 contains no attachment for the safety shield 10 to the head of user 22. This contrasts with shield 13 (FIG. 9) which has points of attachment of the shield to the back of the head 15, the top of the head 14, and the front of the head 16, as well as the band 20 that surrounds the head resulting in headaches, and stress to the user 22, because of the weight, and pressure applied to these points by the face shield 13. The resulting increase in comfort from wearing the safety shield 10 will improve safety of the workplace by reducing worker fatigue, and encouraging more worker use of safety shields. The safety shield 10 shown in FIG. 8 demonstrates a more extensive facial, and upper body protection system that provides the user 22 with a much wider range of protection (to include the upper thorax, facial, and anterior regions) from the projectiles 19 than the face shield 13 provides. The safety shield 10 will not only provide the aforementioned protection, but also makes available shielding from projectiles 19 that come toward the wearer at bench top level 21, the side of the head at eye level or below (to include cheeks, ears, and temple regions), and other anterior angles which might strike the upper thorax and throat region. The aforementioned projectiles 19 may include, but are not limited to biological, chemical, and physical matter that may take the form of solids, liquids, or aerosols.

Figure 9:
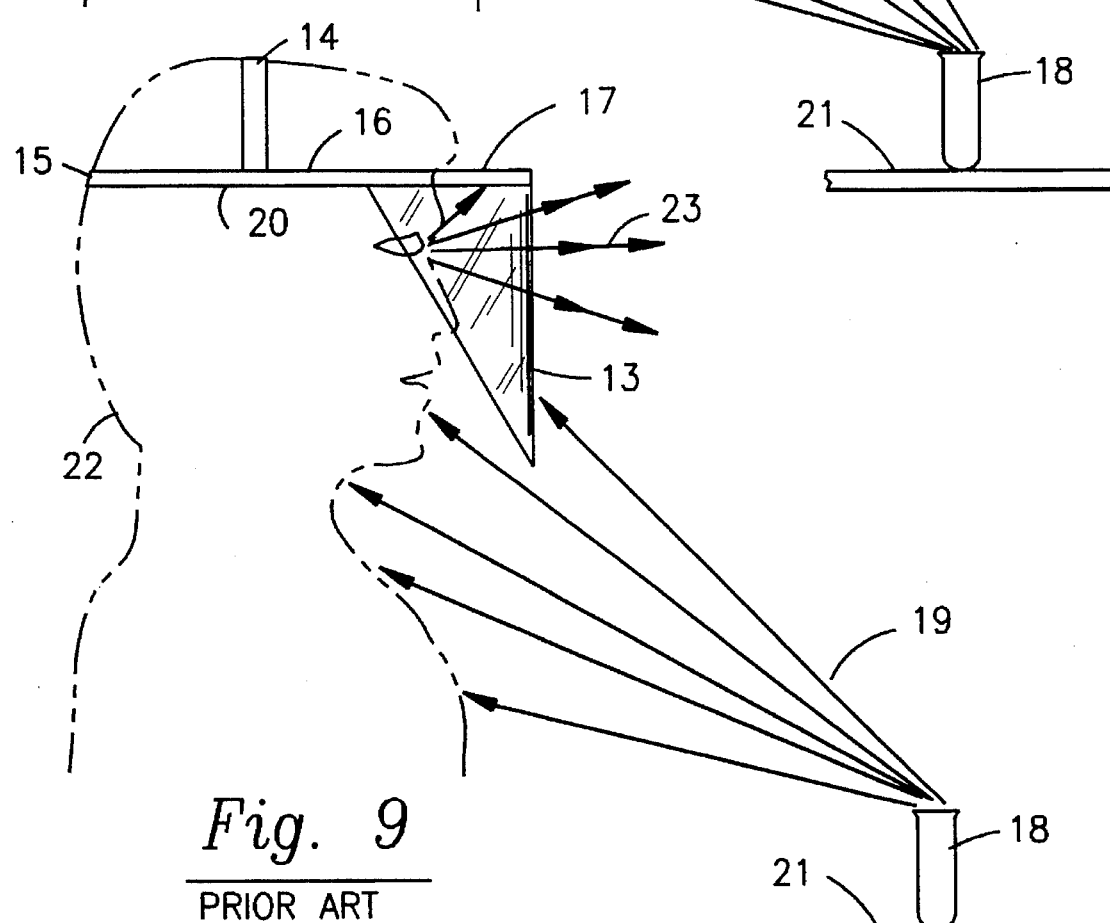

Note that FIG. 8 illustrates the unrestricted vision 23 of the user 22 of the safety shield 10 as compared to the impaired vision 23 (above eye level) of the user 22 of the face shield 13 caused by the lip 17 of the face shield 13 that extends outward from the face of the user 22 in FIG. 9. The safety of the wearer 22 is enhanced by the safety shield 10 via the improved range of vision 23 versus the range of vision 23 allowed by the previous art as illustrated in FIG. 11.

FIG. 9 again illustrates the 'lip' 17 used by previous art to extend shield 13 out in front of user's face 22. This lip 17 acts as a fulcrum yielding a downward force that pulls the shield 13 off of the user's head 22. This downward force requires the user 22 to tighten the headband 20 to prevent shield 13 from falling off. This downward force also applies downward pressure to band 14, and consequently to the top of user's head 22. The pressure from the bands 14, 20 yields resultant pressure to user's head 22 causing headaches, fatigue, and discomfort.

Figure 10:
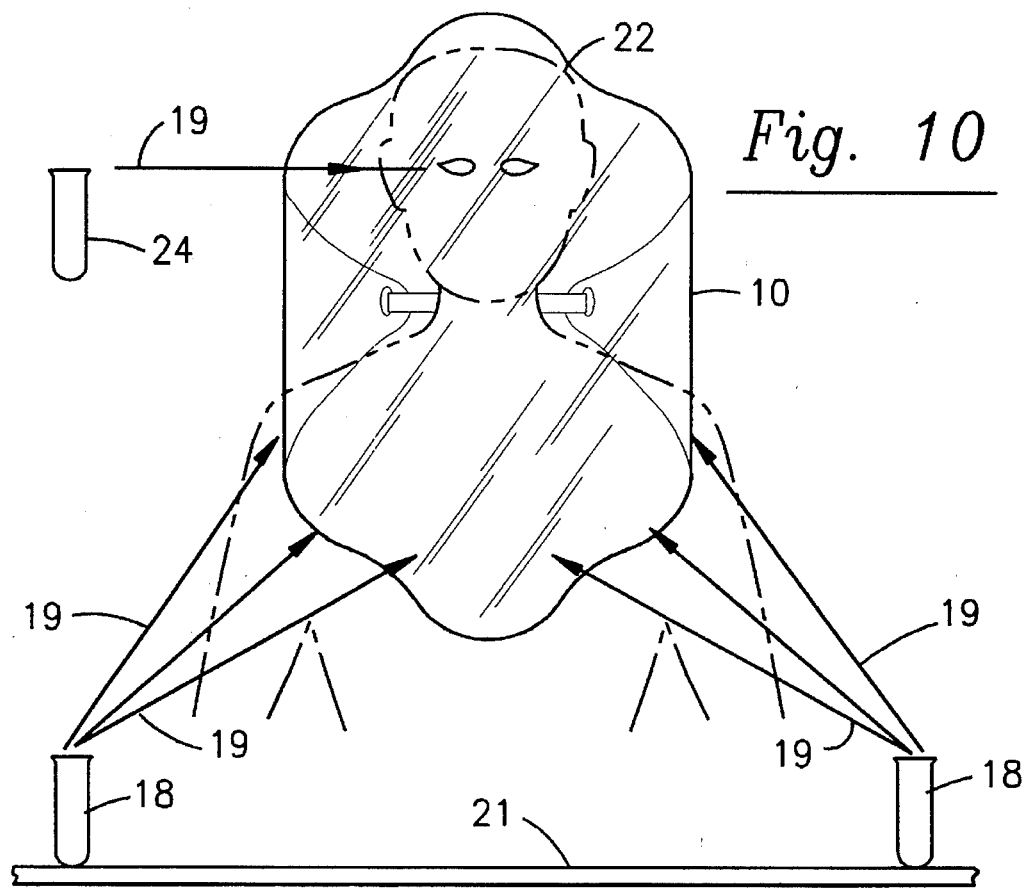
FIG. 10 and FIG. 11 are frontal perspective views showing the relationship between FIG. 10, the safety shield, system and FIG. 11, a face shield of prior art, demonstrating available protection from projectiles coming from various angles.
Figure 11:
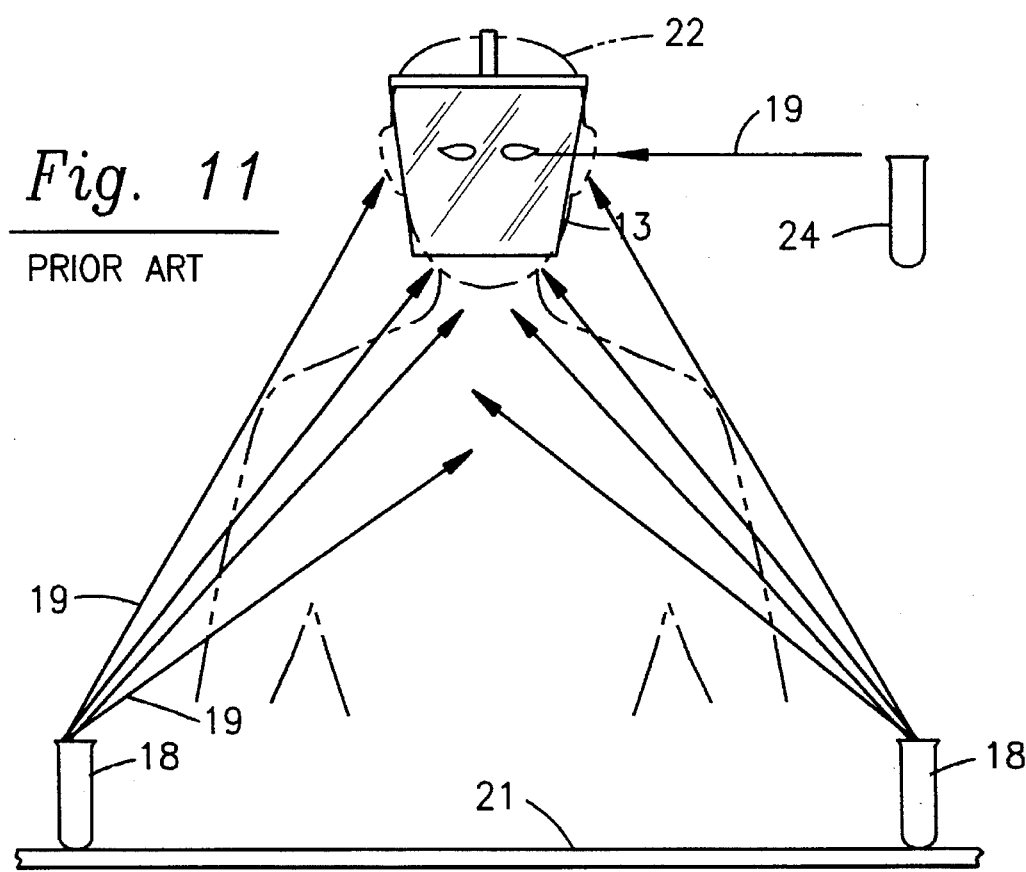

FIG. 10 demonstrates the safety shield's 10 ability to accord the user 22 protection from projectiles 19 that can come from directions oriented in front of the shield at eye level 24 (e.g. vertically oriented, and directly in front at eye level to the shield), which is the only protection afforded by a face shield 13 as shown in FIG. 11. This safety shield 10 not only provides the aforementioned protection, but also makes available shielding from projectiles 19 that come toward the wearer 22 from bench top level 21 (from waist level and up), the side of the head at eye level, or below (to include cheeks, ears, and temple regions), and other anterior angles which might strike the upper thorax, and throat region. The aforementioned projectiles 19, may include, but are not limited to biological, chemical, and physical matter that may take the form of solids, liquids, or aerosols. Also, demonstrated in FIG. 10 is the complete freedom of movement of the head, arms, and body of the user 22.

In agreement with the aforementioned safety shield system is a significant improvement for a more comprehensive facial, and upper body protection system that yields a safer environment for healthcare workers, hobbyists, and industrial employees. The protection afforded by the safety shield is from biological, chemical, and physical matter which may take the form of, but is not limited to liquids, solids, and aerosols.

While the invention has been described in detail in the drawings, and the foregoing description, the same is to be considered as illustrated, and not restricted in character. Thus, it is apparent that many variations, and modifications of the present invention as herein set forth may be made without departing from the spirit, and scope thereof. The specific embodiments are given by way of example only, and the invention is limited only by the terms of the appended claims.

What is claimed is:

1. A one piece portable safety shield free from attachment to a wearer's head, configured to protect the wearer's upper thorax region and full face from biological or chemical liquids or aerosols and physical projectiles, the safety shield comprising a continuous thin flexible transparent curved body having bottom, top and opposed side edges, the bottom edge conforming in shape to an upper thorax and a shoulder region of the wearer and resting on the wearer's upper thorax and shoulders, the top edge extending beyond the top of the wearer's head, the opposed side edges extending beyond ears of the wearer to a point distal from a front of the curved body, the side edges juxtaposed to each other behind a neck of the wearer, and opposed distal portions of the safety shield with respect to a front of the curved body connected together by an elastic member behind the neck of the wearer to hold the safety shield in position.

* * * * *